(12) United States Patent
Demuth et al.

(10) Patent No.: US 6,500,804 B2
(45) Date of Patent: Dec. 31, 2002

(54) METHOD FOR THE IMPROVEMENT OF ISLET SIGNALING IN DIABETES MELLITUS AND FOR ITS PREVENTION

(75) Inventors: Hans-Ulrich Demuth, Halle (DE); Konrad Glund, Halle (DE)

(73) Assignee: Probiodrug AG (DE)

( * ) Notice: Subject to any disclaimer, the term of this patent is extended or adjusted under 35 U.S.C. 154(b) by 0 days.

(21) Appl. No.: 09/824,622

(22) Filed: Apr. 2, 2001

(65) Prior Publication Data

US 2001/0051646 A1 Dec. 13, 2001

Related U.S. Application Data

(60) Provisional application No. 60/194,061, filed on Mar. 31, 2000.

(51) Int. Cl.[7] ........................ A61K 38/00; A61K 31/425
(52) U.S. Cl. ........................... 514/19; 514/365; 514/866
(58) Field of Search ............................ 514/19, 365, 866

(56) References Cited

U.S. PATENT DOCUMENTS

| | | | |
|---|---|---|---|
| 2,961,377 A | 11/1960 | Shapiro et al. | 167/65 |
| 3,960,949 A | 6/1976 | Ahrens et al. | 260/564 B |
| 4,935,493 A | 6/1990 | Bachovchin et al. | 530/331 |
| 5,433,955 A | 7/1995 | Bredehorst et al. | 424/94.3 |
| 5,462,928 A * | 10/1995 | Bachovchin et al. | 514/19 |
| 5,512,549 A | 4/1996 | Chen et al. | 514/12 |
| 5,614,379 A | 3/1997 | MacKellar | 435/68.1 |
| 5,624,894 A | 4/1997 | Bodor | 514/2 |
| 6,006,753 A | 12/1999 | Efendic | 128/898 |
| 6,201,132 B1 * | 3/2001 | Jenkins et al. | 548/535 |
| 6,303,661 B1 * | 10/2001 | Demuth et al. | 514/866 |
| 2001/0025023 * | 9/2001 | Carr | 514/2 |

FOREIGN PATENT DOCUMENTS

| | | | |
|---|---|---|---|
| DE | 25 42598 A1 | 4/1976 | C07C/129/16 |
| DE | 196 16 486 A1 | 10/1997 | A61K/39/395 |
| FR | 2085665 | 3/1971 | A61K/27/00 |
| FR | 2696740 | 10/1992 | C07D/207/404 |
| JP | 4334357 | 11/1992 | C07C/233/57 |
| WO | WO 93/08259 | 4/1993 | |
| WO | WO 95/11689 | 5/1995 | A61K/37/00 |
| WO | WO 95/15309 | 6/1995 | C07D/207/16 |
| WO | WO 95/29691 | 11/1995 | A61K/38/00 |
| WO | WO 97/40832 | 11/1997 | A61K/31/425 |
| WO | WO 97/45117 | 12/1997 | A61K/31/435 |
| WO | WO 98/22494 | 5/1998 | C07K/5/06 |
| WO | WO00/01849 | 1/2000 | C12Q/1/68 |
| WO | WO 00/53171 | 9/2000 | A61K/31/155 |
| WO | WO01/62266 A2 | 8/2001 | A61K/38/00 |

OTHER PUBLICATIONS

Campbell, I.W. New Antidiabetic Drugs, ed. C.J. Bailey & P.R. Flatt, Smith–Gordon, "Sulphonylureas and metformin: efficacy and inadequacy". 3:33–51 (1990).
Mercla Index, 11th Edition, p. 934.
Martindale The Extra Pharmacopeia, 30th Edition, Pharmaceutical Press, 1993, p. 1619.
Chemical Abstracts, vol. 115. No. 15, Oct. 14, 1991 Columbus, Ohio, US; abstract No. 149947q, Schoen Ekkehard et al: "Dipeptidyl peptidase IV in the immune system. Effects of specific enzyme inhibitors on activity of dipeptidyl peptidase IV and proliferation of human lymphocytes".
Chemical Abstracts, vol. 126, No. 2, Jan. 13, 1997 Columbus, Ohio, US; abstract No. 16161j, Stoeckel A. et al: "Competitive inhibition of proline specific enzymes by amino acid thioxopyrrolidides and thiazolidides".
Chemical Abstracts, vol. 118, No. 25, Jun. 21, 1993 Columbus, Ohio, US; abstract No. 255342k, Hosoda, et al, "Preparation of N–(heterocyclic Carbonyl) Amino Acids and Analogs as Prolyl Endopeptidase Inhibitors", Nov. 20, 1992.
Arai et al: "Synthesis of prolyl endopeptidase inhibitors and evaluation of their structure–activity relationships: in vitro inhibition of prolyl endopeptidase from Canine Brain" Chemical And Pharmaceutical Bulletin., Bd. 41, No. 9, 1993, pp. 1583–1588.
J. Lin et al.: "Inhibition of depeptidyl peptidase IV by fluoroolefin–containing n–peptidyl–O–hydroxylamine peptidomimetics" Proceedings Of The National Academy Of Sciences Of USA, vol. 95, Nov. 1998, pp. 14020–14024.
Korom, S., et al "Inhibition of CD26/dipeptidyl peptidase IV activity in vivo prolongs cardiac allograft survival in rat recipients", Transplantation vol. 63, 1495–1500 No. 10 (1997).
Tanka, S., et al., "Suppression of arthritis by the inhibitors of dipeptidyl peptidase IV". Int. J. Immunopharmacol, vol. 19, No. 1 pp. 15–24, 1997.
Mentlein, R., et al., "Proteolytic processing of neuropeptide Y and peptide YY by dipeptidyl peptidase IV". Regul. Pept. 49, 133–144(1993).
Wetzl, W., et al., "Effects of the CLIP fragment ACTH 20–24 on the duration of REM sleep episodes". Neuropeptides, 31, 41–45 (1997).
Amasheh, S., et al., "Electrophysiological analysis of the function of the mammalian renal peptide transporter expressed in Xenopus Laevis oocytes". J. Physiol. 504, 169–174 (1997).

(List continued on next page.)

Primary Examiner—Kevin E. Weddington
(74) Attorney, Agent, or Firm—Mark A. Hofer; Brown Rudnick Berlack Israels, LLP

(57) ABSTRACT

The present invention discloses a method for therapeutically treating mammals, including but not limited to humans, to increase the relative insulin producing performance of endogenous pancreatic β-cells and to cause differentiation of pancreatic epithelial cells into insulin producing β-cells. Oral administration a DP IV inhibitor causes the active form of GLP-1 to be preserved longer under physiological conditions. The extended presence of GLP-1, in particular in the pancreatic tissue facilitates differentiation and regeneration of the β-cells already present that are in need of repair. These repaired insulin producing cells can contribute to the correction and maintenance of normal physiological glycemic levels.

11 Claims, 7 Drawing Sheets

OTHER PUBLICATIONS

Durinx, C.; et al.; "Reference Values for Plasma Dipepidyl–Pepidase IV activity and their Association with Other Laboratory Parameters". Clin Chem Lab Med, Feb. 2001; 39(2):155–9, 1 page.

Gossrau, R.; "Cytochemistry of Membrane Proteases". Histochem J, Jul. 1985; 17(7):737–71, 1 page.

Hahn, T.; et al.; "Enzyme Histochemical Evidence for the Prescence of Potential Blood Pressure Regulating Proteases in Cultured Villous Explants from Human First Trimester Placentae". Acta Histochem 1993, Dec., 1995 (2):185–92, 1 page.

Heymann, E.; et al.; "Has Dipeptidyl Peptidase IV an Effect on Blood Pressure and Coagulation." Klin Wochenschr, Jan. 2, 1984;62 (1) :2–10, 1 page.

Magyar, C.E.; et al.; "Proximal Tubule Na Transporter Responses are the same during Acute and Chronic Hypertension." Am J Physiol Renal Physiol, Aug. 2000; 279 (2):F358–69, 1 page.

Papies, B.; et al.; "Isoenzyme (Lactate Dehydrogenase, Aspartate Aminotransferase) and Dipeptidyl Peptidase IV Activity Changes in Blood Plasma Likely Indicative of Organ Involvement due to Arterial Hypertension." Cor Vasa, 1991; 33(3):218–26, 1 page.

Qureshi. N.U.; et al., "Endogenous Neuropeptide Y Mediates Vasoconstruction during Endotoxic and Hemorrhagic Shock". Regul Pept, Sep. 25, 1998; 75–76:215–20, 1 page.

Index Nominum, International Drug Directory 1992/1993, Medpharm Scientific Publishers, pp. 728–729.

The Merck Index, $9^{th}$ Edition, 1976, p. 773.

C.J. Bailey et al., *New Antidiabetic Drugs*, Smith–Gordon Nishimura, 1990, p. 36.

* cited by examiner

METHOD FOR THE IMPROVEMENT OF ISLET SIGNALING IN DIABETES MELLITUS AND FOR ITS PREVENTION

CROSS REFERENCES TO RELATED APPLICATIONS

This application claims priority of the U.S. Provisional Patent Application Serial No. 60/194,061 filed Mar. 31, 2000 which is incorporated by reference in its entirety.

BACKGROUND

The pancreas comprises two glandular tissues, one, is a collection of cells that form the exocrine function of the pancreas where these exocrine cells synthesize and release digestive enzymes into the intestine; the second tissue comprises the endocrine function of the pancreas which synthesize and release hormones into the circulation. Of prime importance in the endocrine function of the pancreas, are the β-cells. These cells synthesize and secrete the hormone insulin. The hormone insulin plays a vital role in maintaining normal physiological glycemic levels. There are molecules that are effectors of the endocrine cells of the pancreas. Incretins are an example of such molecules. Incretins potentiate glucose-induced insulin secretion from the pancreas.

Incretins such as glucagon-like peptide-1 (7-36) amide ("GLP-1"; or the lizard analog Exendin-4) and gastric inhibitory polypeptide ("GIP") have been demonstrated to be insulinotropic, i.e., their presence or stabilization can maintain acute glycemic control by their insulin-secretive effects (Demuth, H. U., et al., DE 196 16 486:1–6, 1996; Pauly, R. P. et al., Regul. Pept. 64 (1–3): 148, 1996, the teachings of which are incorporated herein by reference in their entirety). Additionally, it has been demonstrated that GLP-1 acts, as an islet growth hormone by stimulating β-cell proliferation, cell mass increase and by promoting undifferentiated pancreatic cells in specialized cells of the islet of Langerhans. Such cells show improved secretion of insulin and glucagon (Yaekura, K. et al., IN: VIP, PACAP, and Related Peptides, W. G. Forssmann and S. I. Said (eds.), New York: New York Academy of Sciences, 1998, p. 445–450; Buteau, J. et al., Diabetologia 42(7): 856–864, 1999, the entire teachings of which are herein incorporated by reference).

It has been previously proposed to apply exogenous bioactive GLP-1, or its analogs, to either stimulate islet cell regeneration in vivo, or to obtain pancreatic cells from diabetes mellitus patients and to treat such cells ex vivo in tissue culture using bioactive GLP-1. This ex vivo treatment was considered to facilitate regeneration and/or differentiation of islet cells which could then synthesis and secrete insulin or glucagon (Zhou, J. et al., Diabetes, 48(12) :2358–2366, 1999; Xu, G. et al., Diabetes, 48(12) :2270–2276, 1999, the entire teachings of which are herein incorporated by reference).

However, such a treatment regime requires the enteral or parenteral application of bioactive GLP-1 to patients, including the possibility of surgery. It is one aspect to obviate the need for surgical treatment, enteral or parenteral applications of bioactive GLP-1.

SUMMARY

The present invention relates to a novel method in which the reduction of activity in the enzyme Dipeptidyl Peptidase (DP IV or CD 26) or of DP IV- like enzyme activity in the blood of mammals induced by effectors of the enzyme leads as a causal consequence to a reduced degradation of the gastrointestinal polypeptide Glucagon-Like Peptide Amide-1 7-36 (GLP-$1_{7-36}$) (or structurally related functional analogs of this peptide, such as GLP-$1_{7-37}$, or truncated but biologically active fragments of GLP-$1_{7-36}$) by DP IV and DP IV-like enzymes. Such treatment will result in a reduction or delay in the decrease of the concentration of functional active GLP-1 (including GLP-1 -derived) circulating peptide hormones or of their analogs.

As a consequence of the resulting enhanced stability of the endogenous GLP-1 (including GLP-1 -derived) circulating peptides caused by the inhibition of DP IV activity, GLP-1 activity is prolonged resulting in functionally active GLP-1 (including GLP-1-derived) circulating peptide hormones facilitating growth-hormone-like stimulation of pancreatic cells in such a way that these cells proliferate to functionally active cells of the Islets of Langerhans. Additionally, insensitive pancreatic cells or impaired pancreatic cells may be transformed into functionally active cells of the islets of Langerhans when exposed to GLP-1.

It was expected, that the transformation of insensitive pancreatic cells or impaired pancreatic cells to functionally active cells of the islets of Langerhans results in an increased insulin secretion and in an increased insulin level in blood plasma. Surprisingly, in studies in healthy human volunteers and obese, diabetic Zucker rats, the insulin level decreased after treatment with the DP IV inhibitor isoleucyl thiazolidine hemifumarate (P32/98) (see examples 1 and 2, respectively). Nevertheless, the resulting regeneration of the islets of Langerhans does change the efficacy of endogenous insulin and other islet hormones, such as glucagon, in such a way that stimulation of carbohydrate metabolism of a treated mammal is effected. As a result, the blood glucose level drops below the glucose concentration characteristic for hyperglycemia, as shown in examples 1 and 2. The mechanism triggering these effects is not known in detail. However, this resulting regeneration of the islet cells further effects anomalies of the metabolism including glucosuria, hyperlipidaemia as well as severe metabolic acidoses and Diabetes mellitus, by preventing or alleviating these sequela.

In contrast to other proposed methods known in the art, such as pancreatic cell or tissue transplantation or ex-vivo treatment of pancreatic cells using GLP- 1 or exendin-4 followed by re-implantation of the treated cells, the present invention does not cause or require complicated and costly surgery, and provides an orally available therapy. The instant invention represents a novel approach for lowering the elevated concentration of blood glucose. It is commercially useful and suitable for use in a therapeutic regime, especially concerning human disease, many of which are caused by prolonged elevated or blood glucose levels.

BRIEF DESCRIPTION OF THE FIGURES

Further understanding of the instant invention may be had by reference to the figures wherein.

DETAILED DESCRIPTION

Figure 1:
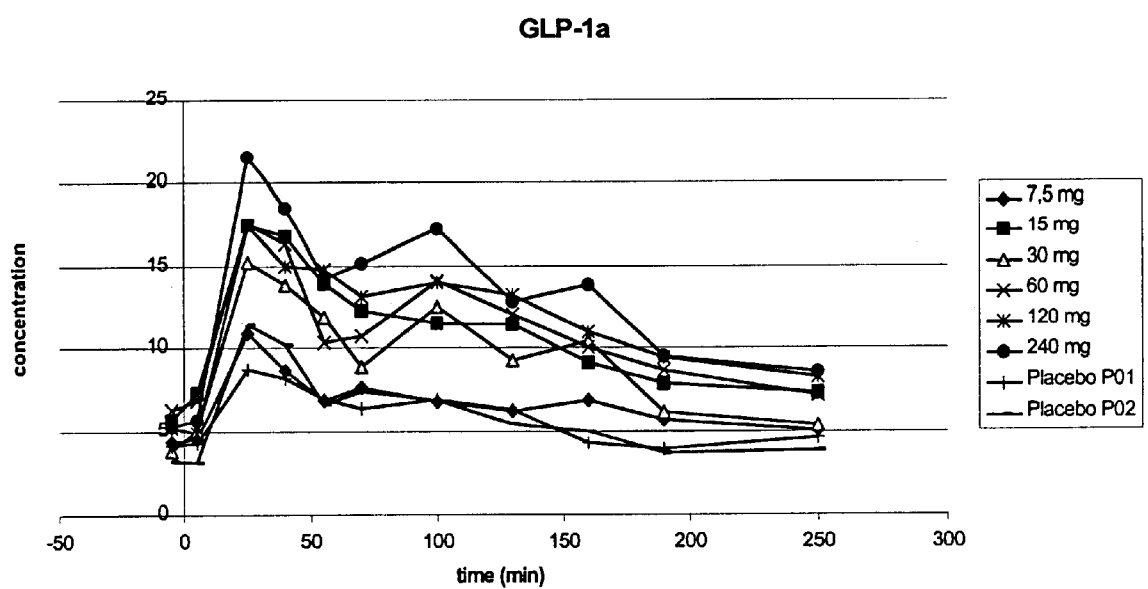
FIG. 1 is a graphical representation of the time-dependency of circulating bioactive GLP-1 in humans (n=36) depending on the orally applied DP IV-inhibitor formulation P32/98.

The present invention pertains to a novel method for differentiating and/or reconstituting pancreatic cells. The resulting regeneration of the islet cells of Langerhans will positively affect the synthesis and release of endogenous insulin and other islet hormones, such as glucagon, in such a manner that the stimulation of carbohydrate metabolism will be effected.

Glucose-induced insulin secretion is modulated by a number of hormones and neurotransmitters. Of specific interest are the two gut hormones, glucagon-like peptide-1 (GLP-1) and gastric inhibitory peptide (GIP), both of which are insulinotropic agents. Insulinotropic agents can stimulate, or cause the stimulation of, the synthesis or expression of the hormone insulin.

GLP-1 is a potent intestinal insulinotropic agent that augments insulin secretion and acutely lowers glucose levels, including levels observed in Type I and Type II diabetes. GLP-1 is formed by alternative tissue-specific cleavages in the L cells of the intestine, the α-cells of the endocrine pancreas, and neurons in the brain. GIP is synthesized and released from the duodenum and proximal jejunum postprandially. Its release depends upon several factors including meal content and pre-existing health status. It was initially discovered and named for its gastric acid inhibitory properties. However, as research into this hormone has progressed, more relevant physiological roles have been elucidated. Specifically, GIP is an insulinotropic agent with a stimulatory effect on insulin synthesis and release.

DP IV is an enzyme that is an exopeptidase which selectively cleaves peptides after penultimate N-terminal proline and alanine residues. Endogenous substrates for this enzyme include the incretins, such as glucose-dependent insulinotropic polypeptides, like GIP and GLP-1. In the presence of DP IV, these hormones are enzymatically reduced to inactive forms. The inactive form of GIP and GLP cannot induce insulin secretion, thus blood glucose levels are elevated, especially in the hyperglycemic state. Elevated blood glucose levels have been associated with many different pathologies, including diabetes mellitus (Type 1 and 2) and the sequelae accompanying diabetes mellitus.

It has also been discovered that DP IV plays a role in T-cell-mediated immune responses, for example, in transplantations. Inhibition of DP IV has been demonstrated to prolong cardiac allografts. Additionally, the inhibition of DP IV has contributed to the suppression of rheumatoid arthritis. DP IV has also been attributed a role in HIV's penetration into T-cells (T-helper cells).

Agents such as N-(N'-substituted glycyl)-2-cyanopyrrolidines, L-threo-isoleucyl thiazolidine (P32/98), L-allo-isoleucyl thiazolidine, L-threo-isoleucyl pyrrolidine, and L-allo-isoleucyl pyrrolidine have been developed which inhibit the enzymatic activity of DP IV are described in US 6,001,155, WO 99/61431, WO 99/67278, WO 99/67279, DE 198 34 591, WO 97/40832, DE 196 16 486 C 2, WO 98/19998, WO 00/07617, WO 99/38501, and WO 99/46272, the teachings of which are herein incorporated by reference in their entirety. The goal of these agents is to inhibit DP IV, and by doing so, to lower blood glucose levels thereby effectively treating hyperglycemia and attendant diseases associated with elevated levels of glucose in the blood. The inventors hereof have surprisingly discovered that such agents can be advantageously employed for an entirely different therapeutic purpose, then previously known by those skilled in the art.

Diseases which characteristically demonstrate hyperglycemia include diseases such as Diabetes mellitus, Type I and II. Diabetes may generally be characterized as an insufficient hormone output by the pancreatic β-cells. Normally, these cells synthesize and secrete the hormone insulin. In Type I diabetes, this insufficiency is due to destruction of the beta cells by an autoimmune process. Type II diabetes is primarily due to a combination of beta cell deficiency and peripheral insulin resistance. In the diabetic patient, the number of beta cells is reduced so not only is there a concern regarding the ability of beta cells to synthesize and release physiological insulin, but there is also a concern surrounding the critical mass of these insulin producing pancreatic cells. Loss of beta cells is known to occur with the presence of diabetes. With the loss of these insulin producing cells, there exists a strain on the endocrine function of the pancreas to produce, for example, insulin. With the loss in insulin output, pathological processes due to hyperglycemia can become exacerbated.

GLP-1 acts as an islet growth hormone by stimulating β-cell proliferation, cell mass increase and by promoting undifferentiated pancreatic cells in specialized cells of the islet of Langerhans. Such GLP-1 exposed pancreatic cells show improved secretion of insulin and glucagon (Yaekura, K. et al., IN: VIP, PACAP, and Related Peptides, W. G. Forssmann and S. I. Said (eds.), New York: New York Academy of Sciences, 1998, p. 445–450; Buteau, J. et al., Diabetologia 42(7): 856–864, 1999). The inventors have discovered that it is desirable to increase GLP-1's half-life to thereby facilitate reconstitution of the pancreatic beta cells. The inventors have also discovered a method whereby catabolism of GLP-1 maybe attenuated in order to improve reconstitution of the pancreatic cells.

The method of the present invention for treating hyperglycemia in a mammal, including but not limited to humans, comprises potentiating GLP-1's presence by inhibiting DP IV, or related enzyme activities, using an inhibitor of the enzyme. Oral administration of a DP IV inhibitor may be preferable in most circumstances. However, other routes of administration are envisaged in the present invention. By inhibiting the DP IV enzyme activity, the half-life of the active form of GLP-1 will be appreciably extended and maintained under physiological conditions. The extended presence of active GLP-1, in particular in the pancreatic tissue, will facilitate the differentiation of pancreatic epithelial cells into pancreatic effector cells, like insulin producing β-cells. Moreover, prolonging GLP-1's physiologically active presence in pancreatic tissue will facilitate the regeneration of those β-cells which are already present but in need of repair. Surprisingly, this effect is only observable after repeated dosing (see example 2). Since withdrawel of the medication resuls in restoration of the prior metabolic state, subchronic or chronic dosing of the DP IV effector is needed to maintain the achieved improved glycemia. These repaired insulin producing cells can then effectively contribute to the correction and maintenance of normal physiological glycemic levels.

In the present invention endogenous GLP-1 is synthesized and released in the normal physiological routes. Ingestion of a meal can stimulate the release of GLP-1. Alternatively, glucose or its analog can be given orally in the form of a pharmaceutically acceptable carrier (for example, a "sugar pill") in order to stimulate release of endogenous GLP-1. Such glucose may be taken, before, concurrently or following administration of the DP IV inhibitors.

This invention also provides pharmaceutical compositions. Such compositions comprise a therapeutically (or prophylactically) effective amount of the inhibitor (and/or a sugar pill to accompany administration of a DP IV inhibitor), and a pharmaceutically acceptable carrier or excipient. The carrier and composition are produced under good laboratory practices conditions and are sterile. The formulation is ideally selected to suit the mode of administration, in accordance with conventional practice.

Suitable pharmaceutically acceptable carriers include but are not limited to water, salt solutions (for example, NaCl), alcohols, gum arabic, vegetable oils, benzyl alcohols, polyethylene glycols, gelatin, carbohydrates such as lactose, amylose or starch, magnesium stearate, talc, viscous paraffin, perfume oil, fatty acid esters, hydroxymethylcellulose, polyvinyl pyrolidone, etc. The pharmaceutical preparations can be sterilized and if desired mixed with auxiliary agents, for example, lubricants, preservatives, stabilizers, wetting agents, emulsifiers, salts for influencing osmotic pressure, buffers, coloring, flavoring and/or aromatic substances and the like which do not deleteriously react with the active compounds, but which improve stability manufacturability and/or aesthetic appeal.

The compositions, if desired, can also contain minor amounts of wetting or emulsifying agents, or pH buffering agents. In addition, the composition can be a liquid solution, suspension, emulsion, tablet, pill, capsule, sustained release formulation, or powder. In addition, the composition can be formulated as a suppository, with traditional binders and carriers such as triglycerides. Oral formulations can include standard carriers such as pharmaceutical grades of mannitol, lactose, starch, magnesium stearate, polyvinyl pyrollidone, sodium saccharine, cellulose, magnesium carbonate etc.

Further, the compositions can be formulated in accordance with methods that are well known in the art of pharmaceutical composition adapted for intravenous administration to human beings. Typically, compositions for intravenous administration are sterile isotonic aqueous buffered solution. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active compound. Where the composition is to be administered by infusion, it can be dispensed with an infusion bottle containing sterile pharmaceutical grade water, saline or dextrose/water. Where the composition is administered by injection, an ampoule of sterile water for injection or saline can be provided so that the ingredients may be mixed just prior to administration.

Finally, compositions of the invention can be formulated as neutral or salt forms. Pharmaceutically acceptable salts include those formed with free amino groups such as those derived from hydrochloric, phosphoric, acetic, oxalic, tartaric acid, etc., and those derived from sodium, potassium, ammonium, calcium, ferric hydroxides, isopropylamine, triethylamine, 2-ethylamino ethanol, histidine, procaine, and other salt forms that are well known in the art.

The amount of the invention's composition which will be effective in the treatment of a particular disorder or condition will depend on the nature of the disorder or condition, and can be determined by standard clinical techniques. In addition, in vitro and/or in vivo assays may optionally be employed to help identify optimal dosage ranges. The precise dose to be employed in the formulation will also depend on the route of administration, and the seriousness of the disease or disorder. The dose should be decided according to the judgement of the practitioner taking into consideration each patient's circumstances.

It will be readily understood by the skilled artisan that numerous alterations may be made to the examples and instructions given herein including the generation of different DP IV inhibitors and alternate therapeutic compositions without departing from either the spirit or scope of the present invention. The following examples as described are not intended to be construed as limiting the scope of the present invention.

EXAMPLES

Example 1

The DP IV-inhibitor P32/98 is actively transported via the PepT1 intestinal peptide transporter. The fast and active transport of P32/98 through the intestinal mucosa is responsible for its fast onset. The $t_{max}$ is a prerequisite for the efficient targeting of dipetidylpeptidase IV (DP IV). Oral administration of P32/98 results in a maximum target inhibition 15 to 20 min and 30 to 40 min after ingestion in rats and men, respectively. Therefore, the DP IV-inhibitor should be given 10–20 min prior to glucose or meal intake.

In the first-human study with P32/98, pharmacodynamic parameters like insulin concentration and GLP-1 concentration in the plasma and blood glucose were investigated in 36 healthy male volunteers. The oral dosing of P32/98 was in the following concentrations: 7.5 mg, 15 mg, 30 mg, 60 mg, 120 mg and 240 mg. The results of above pharmacodynamic parameters are summarized below in Table 1.

The 36 healthy male subjects were divided into 3 individual groups with each group containing 12 subjects. In each individual group 9 subjects received active drug P32/98 and 3 received placebo. The subjects receiving active drug were dosed twice, at different periods and at different strengths. The strengths of the P32/98 received within the groups were as follows:

group I received 7.5 mg and 60 mg;

group II received 15 mg and 120 mg; and group III received 30 mg and 240 mg.

The subjects in all groups who were receiving placebo were given placebo at both dosing intervals.

A pre-study examination of the subjects was conducted within 3–14 days before their participation in the study. A second portion of the study comprised an experimental phase and entailed six single-dose treatments of ascending concentrations of P32/98, (periods 1 to 6; Table 2) which concluded with a follow up examination. Each subject participated in the pre-study and experimental phase, which were separated by a washout phase of at least 5 days. The follow-up examination was done at least 7 days after the last dose of study drug. The study procedures of the six periods were identical, except for the dose under investigation.

Methods

Oral glucose tolerance test ("OGTT"): Subjects were required to be in a fasting state for at least 12 hours and comply with a carbohydrate-rich diet 3 days before each OGTT. At each glucose tolerance test, subjects ingested 300 mL of a mono-/disaccharid solution equivalent to 75 g glucose (Dextro®O.G.-T, Boehringer Mannheim, FRG). Blood samples (1.2 mL into sodium fluoride tubes) were taken immediately prior to glucose intake and at 30, 60, 90 and 120 min thereafter. Any glucose concentration above 126 mg/dl (7.0 mmol/L) at 0 min and 120 min was considered to be in a pathological glucose tolerance state.

An extended OGTT was performed on Day 1 of each dosing period. Subjects ingested 300 mL of a mono-/disaccharid solution equivalent to 75 g glucose. Blood samples (1.2 mL) were taken at the following intervals:

1) 5 minutes prior to glucose intake;
2) at 5, 15, 30, 45, 60, 75, 90, 120, 150 and 180 min after glucose intake;
3) 4, 12, and 24 and 48 hours after glucose intake Additionally other pharmacodynamic assessments that are well known in the art were taken.

Insulin: 4.7 ml blood was collected into 4.9 ml EDTA-tubes. Samples were centrifuged (1500 g, 10 min) and stored frozen at −70° C. until laboratory analysis.

Glucose: 1.2 ml blood was collected into 1.2 ml sodium fluoride tubes. Plasma samples were centrifuged at 1500 g for 10 min and stored frozen at −70° C. until laboratory analysis. GLP-1: 2.7 ml blood was collected in EDTA tubes and placed on ice or refrigerated, to which a dipeptidyl peptidase IV-inhibitor was added. The inhibitor was prepared in advance by researchers. Blood was collected in tubes and centrifuged immediately at 1000 g for 10 min in refrigerated centrifuge or the blood was placed in ice and centrifuged within 1 hour and aliquoted into equal samples. Blood was stored in appropriate aliquots at −70° C. (to avoid multiple freezing/thawing cycles) until laboratory analysis.

Results

Active GLP-1 concentrations A dose-dependent effect of P32/98 compared to placebo was found. Overall individual concentrations varied between 2–68 pmol/l. Pre-dose group means were between 3.77±2.62 pmol/l and 6.67±9.43 pmol/l and increased by up to 4.22 and 7.66 pmol/l following use of a placebo, but by 11.6 pmol/l (15 mg) and 15.99 pmol/l (240 mg P32/98) following use of the inhibitor. If the relative mean increase is estimated from the absolute concentrations, active GLP-1 concentrations increased by approximately 200–300% after placebo treatment, but by approximately 300–400% following P32/98 treatment. The absolute increase in medians after 15–240 mg P32/98 was 2–3-fold higher compared with placebo and the 7.5-mg dose (see Table 1) and roughly indicated a dose-response relationship. An increase above pre-dose values was present up to approximately 3–4 hours relative to the P32/98 dose. Insulin concentrations showed an overall individual range of values between 3.40 and 155.1 μIU/ml. Mean (±SD) pre-dose concentrations varied between 7.96±1.92 μIU/ml (30 mg) and 11.93±2.91 μIU/ml (60 mg P32/98). Following the ingestion of 75 g of glucose at 10 min post-dose P32/98/placebo, mean insulin concentrations increased by 30.12 μIU/ml (120 mg P32/98) to 56.92 μIU/ml (30-mg group) within 40–55 min. There was no apparent difference between placebo and the P32/98 dosing groups and, again, no evidence for a dose-dependent effect of P32/98. Interestingly, the absolute increase in insulin concentration was lowest in the two highest P32/98 dosing groups (see Table 1). The insulin concentrations were elevated for 3–4 hours in all study groups including placebo.

Glucose concentrations showed an overall range between 2.47 to 11.7 mmol/l in the fasted state, during OGGT or after meals across all study subjects. Mean pre-dose concentrations between 4.55±0.41 (15 mg) and 4.83±0.30 mmol/l (7.5 mg P32/98) closely matched each other and showed little variation. Mean maximum concentrations were reached within 40–55 min post-dose, i.e. within 30–45 min after the 75 g glucose dose. Absolute mean concentrations were highest in the two placebo and 7.5 mg P32/98 dosing groups. The lowest absolute means were obtained from the 15 mg, 60 mg an d-240 mg dosing groups. The corresponding mean changes ranged between 3.44 to 4.21 mmol/l and 1.71 to 3.41 mmol/l, respectively, and closely matched the medians provided in Table 1. Although no perfect dose-dependency was observed, these results indicate a lower increase in glucose concentrations with increasing doses from 15–240 mg of P32/98 compared with placebo.

TABLE 1

Maximum Changes in Pharmacodynamic Parameters (0–12h, medians)

|  | Placebo (1–3) | 7.5 mg P32/98 | 15 mg P32/98 | 30 mg P32/98 | Placebo (4–6) | 60 mg P32/98 | 120 mg P32/98 | 240 mg P32/98 |
|---|---|---|---|---|---|---|---|---|
| GLP-1, active [pmol/l] | 3.90 0:25h | 4.10 1:10h | 10.00 0:25h | 10.60 0:40h | 5.30 0:40 | 12.20 0:25h | 11.10 0:25h | 14.50 0:25h |
| insulin [μIU/ml] | 46.29 0:55h | 41.86 0:55h | 29.67 0:55h | 59.84 0:40h | 42.90 0:40h | 43.35 0:40h | 28.63 0:40h | 33.36 0:40h |
| glucose [mmol/l] | 3.43 0:55h | 4.66 0:55h | 2.43 0:55h | 3.38 0:40h | 5.33 0:55h | 2.92 0:40h | 2.39 0:40h | 1.73 0:40h |

TABLE 2

Corrected C$_{max}$ and AUC of Glucose Concentrations 0–3 h After OGTT

| | AUC$_{0\to 180\ min}$ [mmol*min/l] | | | C$_{max}$ [mmol] | | |
|---|---|---|---|---|---|---|
| | Mean ± SD | Estimate[1] | 95%-CI | Mean ± SD | Estimate | 95%-CI |
| Periods 1–3 | | | | | | |
| Placebo | 223.9 ± 143.3 | | | 4.16 ± 1.10 | | |
| 7.5 mg P32/98 | 299.7 ± 111.4 | 75.8 | −48.1 – 199.7 | 4.94 ± 1.58 | 0.78 | −0.40 – 1.96 |
| 15 mg P32/98 | 130.9 ± 125.2 | −93.0 | −216.9 – 30.9 | 2.92 ± 1.10 | −1.24* | −2.43 – −0.06 |
| 30 mg P32/98 | 116.1 ± 134.0 | −107.7 | −231.6 – 16.2 | 3.26 ± 1.07 | −0.90 | −2.08 – 0.28 |
| Periods 4–6 | | | | | | |
| Placebo | 252.9 ± 103.3 | | | 4.91 ± 1.14 | | |
| 60 mg P32/98 | 151.8 ± 99.2 | −101.1 | −204.8 – 2.6 | 3.50 ± 1.66 | −1.41* | −2.66 – −0.17 |
| 120 mg P32/98 | 126.7 ± 147.3 | −126.1* | −229.8 – 22.4 | 3.09 ± 1.47 | −1.82** | −3.07 – −0.58 |
| 240 mg P32/98 | 24.7 ± 66.6 | −228.2*** | −331.8 – −124–5 | 1.99 ± 0.69 | −2.92*** | −4.16 – −1.68 |

[1]Results from ANOVA comparison versus placebo
*p <0.05; p <0.01; *p <0.001

Baseline-corrected mean peak (C$_{max}$) glucose concentrations exceeded 4.0 mmol/l in the two placebo and 7.5 mg P32/98 dosing groups only. These values were also below 3.0 mmol/l in the 15 mg and the 240 mg P32/98 treatment groups. The difference compared to placebo treatment was statistically significant for the 15 mg, 60 mg, 120 mg and 240 mg P32/98 dosing groups, but not for the 7.5 mg and the 30 mg dose groups. Mean baseline-corrected AUC values were >200 mmol*min/l after placebo and 7.5 mg P32/98, but clearly below 200 mmol*min/l following the 15 mg and 240 mg P32/98 doses. The reduction in systemic glucose exposition from the OGTT was statistically significant for the 15 mg, 60 mg, 120 mg and 240 mg P32/98 dosing groups, but not for the 7.5 mg and 30 mg dose groups (see Table 2). The evaluation of baseline-corrected values was very similar to those obtained from uncorrected data. Thus, the data indicated a clearly lower glucose exposition after the OGTT in P32/98 treated healthy subjects, which was an approximate, but not perfect dose-dependent indication.

Conclusions

Figure 2:
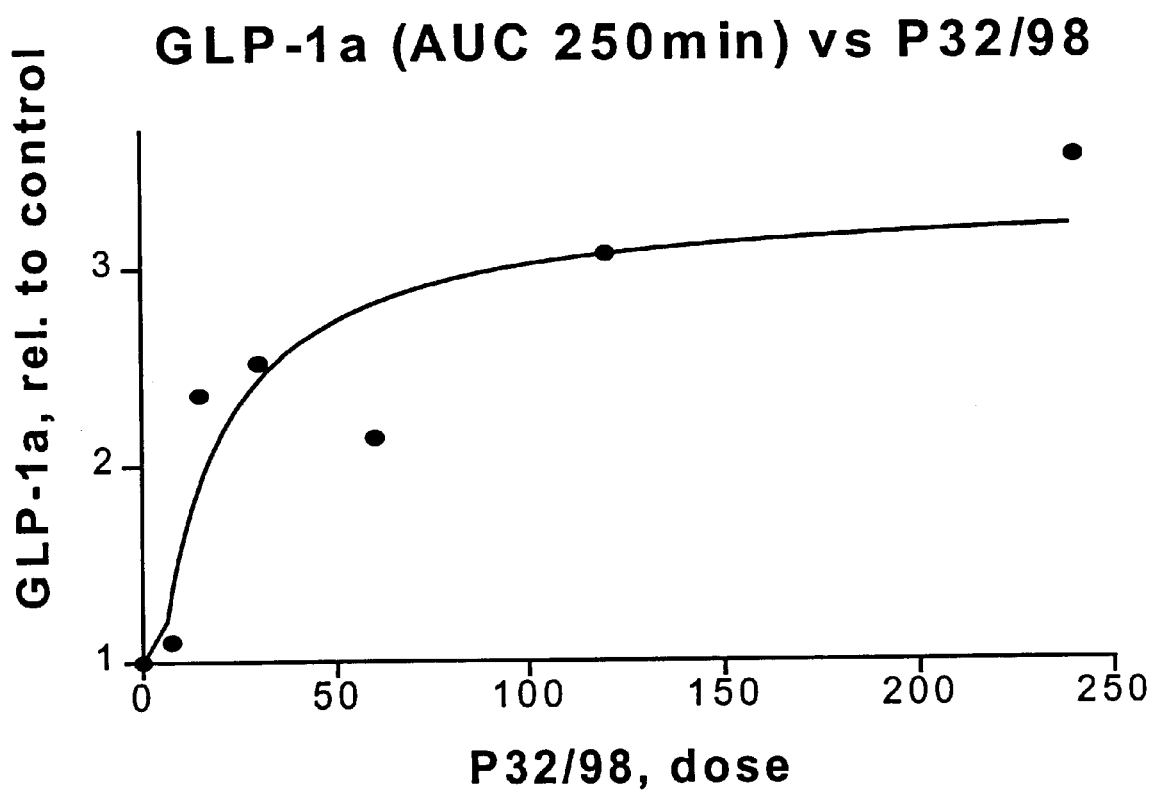
FIG. 2 is a graph representing the dependency of the AUC of circulating bioactive GLP-1 in humans (n=36) on the orally applied DP IV-inhibitor formulation P32/98.
Figure 3:
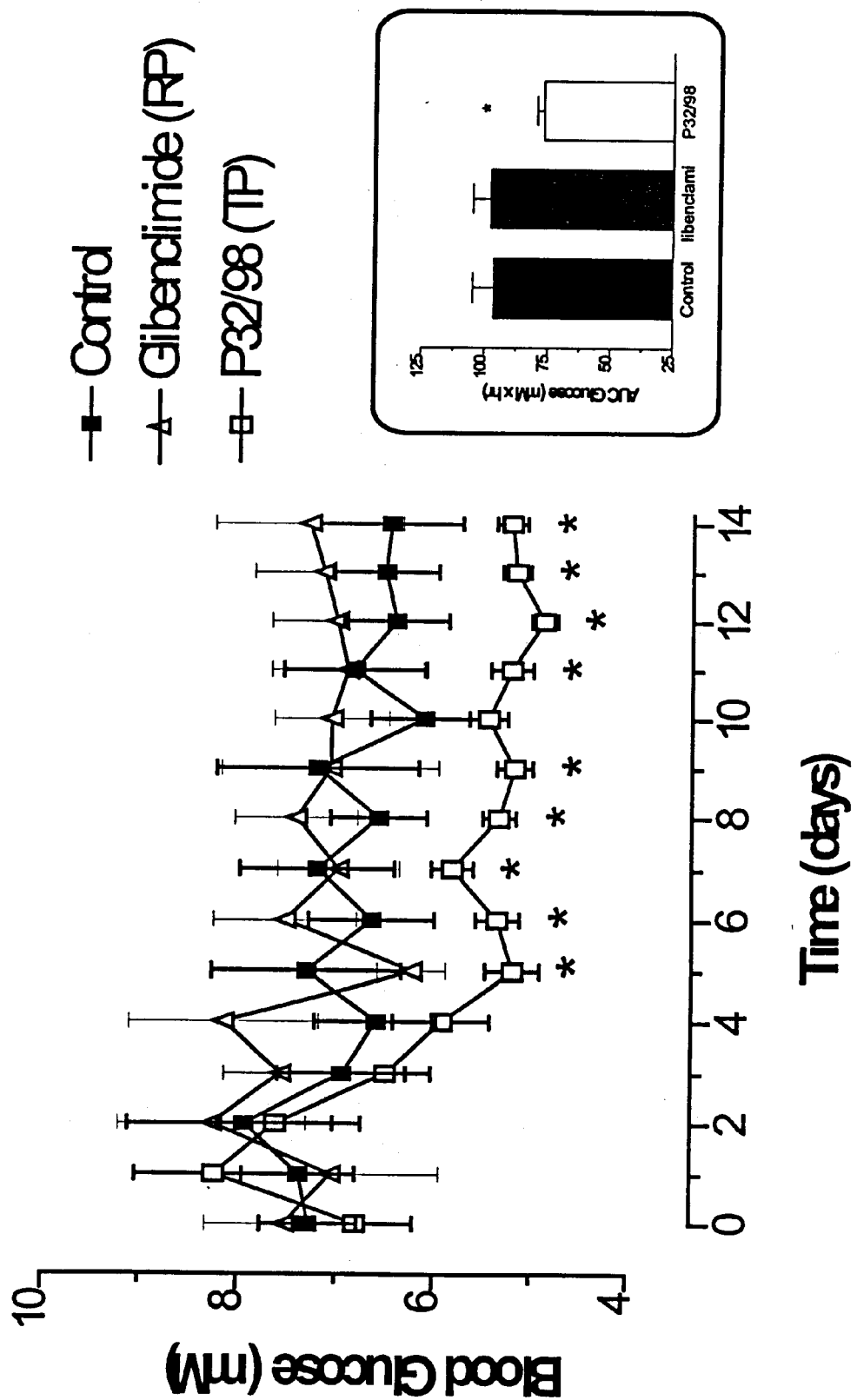
FIG. 3 is a graphical representation showing the improvement of morning blood-glucose (MBG) after subchronic monotherapeutic application of 8.7 mg/kg/d of P32/98 to obese, diabetic fa/fa rats.

Results of this study allow the following pharmacodynamic conclusions:

Active GLP-1 increased by approximately 300–400% following P32/98 treatment 10 min prior to OGTT, but no effect discernible from placebo treatment was seen for the 7.5-mg dose level (see FIGS. 1 and 2). Insulin concentrations appeared to be decreased at doses of 120–240 mg following stimulation with 75 g glucose. During the OGTT in healthy subjects, glucose concentrations showed a significantly lower increase after P32/98 treatment (15–240 mg) compared with placebo, which was related to the P32/98 dose.

Example 2

In the obese Zucker rat, P32/98 nutrient-dependent supports initial insulin secretion. However, during a subchronic treatment, P32/98 reduces the total daily insulin secretion. Compared to a control glibenclamide, which increases insulin output by 27%, P32/98 causes an economization of insulin by saving 45% compared to the control.

Testing was undertaken to determine whether P32/98 is a prime candidate to influence glucose tolerance in vivo by increasing the circulating half-lifes of the incretins GIP and GLP-1. Comparative studies were carried out with glibenclamide (Maninil® Berlin-Chemie, Berlin, Germany) as reference substance. Glibenclamide is one of the most effective drugs for reducing blood glucose in Type 2 diabetic patients and one of the most frequently prescribed sulphonylureas.

Male Zucker fa/fa rats, which exhibit abnormalities in glucose metabolism and are a well established animal model for Type 2 diabetes, were investigated in the following way:

P32/98 and glibenclamide were given once daily before food intake for a period of 21 days. The parameters monitored were morning blood glucose and plasma insulin levels. In a day-night profile, glycemia and insulinaemia were monitored from day 16 to day 17. An OGTT was performed finally on day 21 to monitor blood glucose and plasma insulin kinetics to assess changes in glucose tolerance. Glibenclamide (DAB 1996; R011150/33372) was donated by Berlin-Chemie (Berlin, Germany). Male Zucker (fa/fa) rats of the body weight class of 300 g were purchased from Charles River (Sulzfeld, Germany).

Methods

Housing Conditions: Animals were kept single-housed under conventional conditions with controlled temperature (22±2° C.) on a 12/12 hours light/dark cycle (light on at 06:00 a.m.). Standard pellets (ssniff®, Soest, Germany) and tap water acidified with HCl were allowed ad libitum.

Catheterization of Carotid Artery: After one week of adaptation carotid catheters were implanted in the rats under general anesthesia (injection of 0.25 ml/kg i.p. Rompun® [2%], Bayer, Germany) and 0.5 ml/kg i.p. Velonarkon® (Arzneimittelwerk Dresden, Germany). The animals were allowed to recover for one week. The catheter was flushed with heparin-saline (100 IU/ml) three times per week.

Repeated Dosing: 30 male non-diabetic Wistar and 30 male diabetic Zucker rats were randomized to RP (Reference Product: glibenclamide)-, TP- (Test Product: P32/98) and CO-(Control) groups (N=10 per group). Thereafter, the non-diabetic Wistar rats were treated orally once daily with RP (5 mg/kg b.w.) or TP (21.61 mg/kg b.w.) and the diabetic Zucker rats were treated orally once daily with RP (1 mg/kg b.w.) or TP (21.61 mg/kg b.w.) for 21 days at 05.00 p.m. (before regular food intake in the dark phase). The controls were given 1% cellulose solution orally (5 ml/kg). Blood samples were taken every morning at 07.30 a.m. from tail veins for measurement of blood glucose and plasma insulin. The last blood samples of this part of the program were taken at 07.30 a. m. on the 15$^{th}$ day to measure blood glucose and plasma insulin. The oral drug therapy was continued for one week. Recording the day-night profile under the above therapy blood glucose (Δt=3 h) and plasma insulin (Δt=3–6 h) were monitored from day 16 (at 05.00 p.m. beginning) to day 17 (at 02.00 p.m. end).

OGTT: A final OGTT was performed on day 21 with blood sampling from the tail vein. Blood samples from the tail vein were taken at –12 h (the night before day 21), at 0 min (immediately before the beginning of OGTT), at 10, 20, 30, 40, 50, 60, 80, 100 and 120 min. Blood samples were taken in 20 μl glass capillaries for blood glucose measurements and in Eppendorf tubes (100 μl). The latter were immediately centrifuged and the plasma fractions were stored at –20° C. for insulin analysis.

Blood glucose: Glucose levels were measured using the glucose oxidase procedure (Super G Glukosemeβgerätebau; Dr. Müller Gerätebau, Freital, Germany).

Plasma insulin: Insulin concentrations were assayed by the antibody RIA method (LINCO Research, Inc. St. Charles, Mo., USA).

Results

Figure 4A:
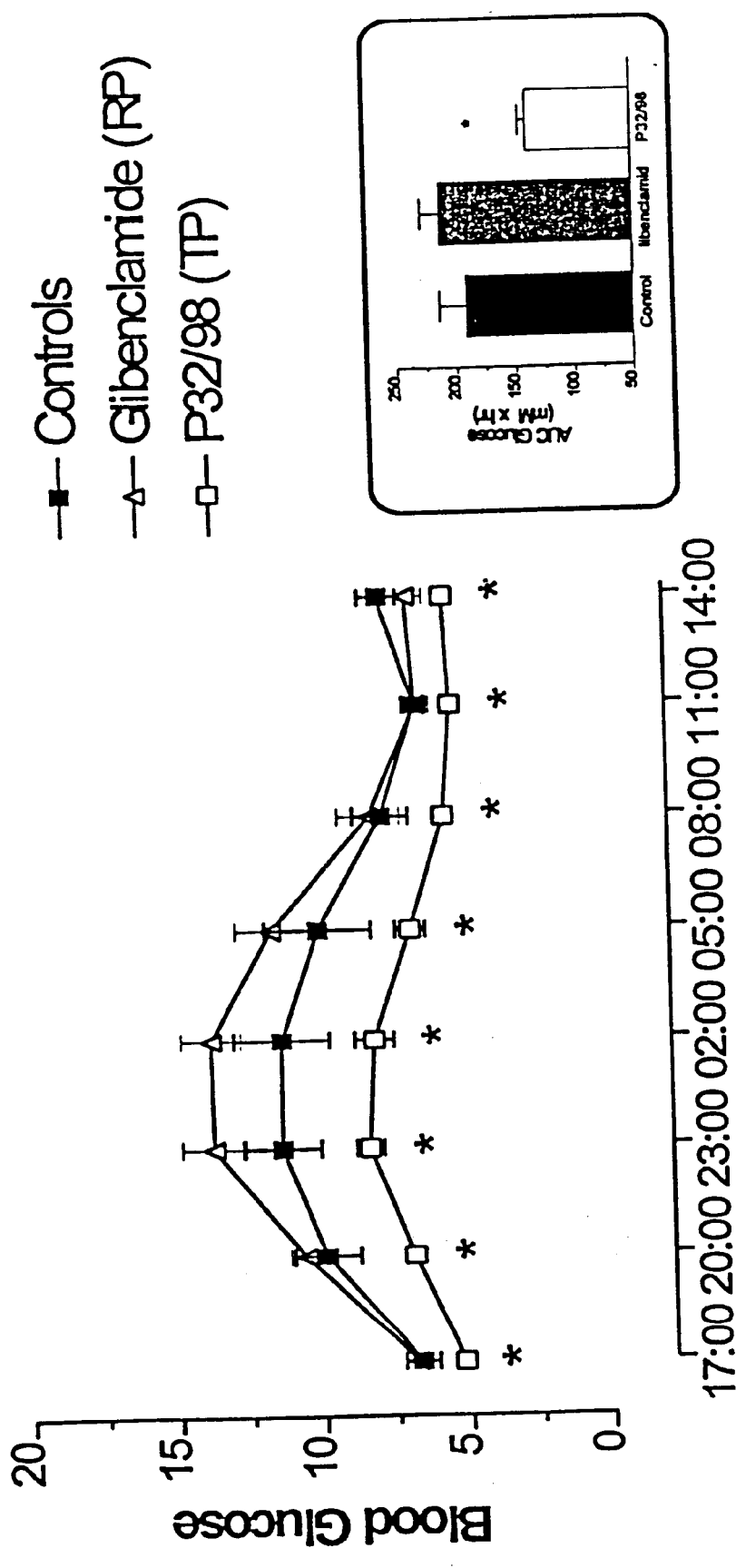
FIG. 4a is a graphical representation showing improved glucose-control due to DP IV-inhibitor treatment after 16-days of treatment in obese diabetic rats

Day-night profile of glycemia (see FIG. 4A): The mean blood glucose concentration in the CO-group on day 16 was 7.78±0.83 mmol/l before drug application at 05.00 p.m.. After oral placebo ingestion and food intake in the dark phase glycemia increased to maximum values of 12.18±1.34 mmol/l at 11.00 p.m. Thereafter, glycemia declined very slowly to the lowest values of 7.27±0.61 mmol/l at 11. a.m., followed by an increase to 8.90±0.92 mmol/l at 02.00 p.m. next day. In the RP-group, a similar picture of glycemia was seen. However, from a comparable mean value of 7.96±1.13 mmol/l at 05.00 p.m. with respect to control animals there was a stronger increase to 14.80±1.46 mmol/l (11.00 p.m.) and thereafter a decline to 7.66±1.22 mmol/l (11.00 a.m.) and a further slight reduction to 7.34±0.77 mmol/l at 02.00 p.m. of the next day, respectively. In the TP-group the Zucker rats had a normal mean blood glucose value of 5.25±0.16 mmol/l at 05.00 p.m. and the individual values were in the range from 4.34 to 6.07 mmol/l. Glycemia showed an increase of about 3 mmol/l to 8.34±0.47 mmol/l at 11.00 p.m. This was followed by a permanent decline to basal values which were reached at 08.00 a.m. (5.64±0.23) and which were maintained at 11.00 a.m. (5.33±0.14 mmol/l) and 02.00 p.m. next day (5.51±0.19 mmol/l), respectively.

Figure 4B:
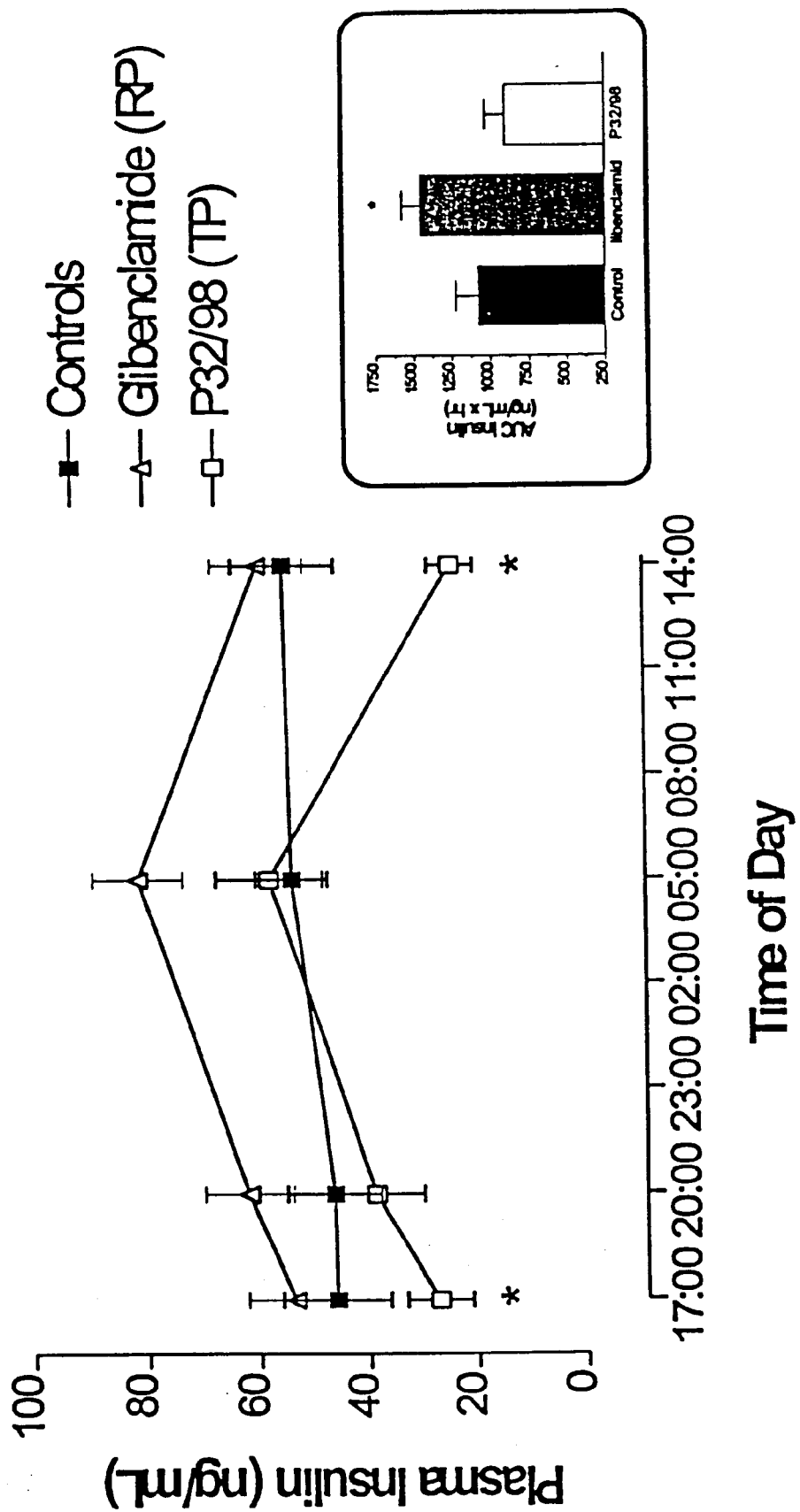
FIG. 4b is a graphical representation showing reduced insulin-secretion due to DP IV-inhibitor treatment after 16 days of treatment in obese diabetic rats.

Day-night profile of insulinemia: (see FIG. 4B): The CO- and RP- Zucker rats were strongly hyperinsulinemic. Insulin showed a variability in mean values at 05.00 p.m. in the CO-group (47.0±8.7 ng/ml), 08.00 p.m. (45.5±7.7 ng/ml), 05.00 a.m. (54.2±5.7 ng/ml) and 02.00 p.m. next day (61.0±10.2 ng/ml; NS) which showed no relation to the excursions of blood glucose. In RP-group in the dark phase from 06.00 p.m. to 06.00 a.m. there was a significant increase in plasma insulin values with a maximum at 5.00 a.m.. This parameter increased from strongly hyperinsulinemic values of 50.0±8.2 ng/ml (05.00 p.m.) via 57.3±8.2 ng/ml (08.00 p.m.) to 76.3±8.6 ng/ml (05.00 a.m.; p<0.01 vs. initial value), which was followed by a decline to 58.3±7.3 ng/ml (02.00 p.m. the next day). In this RP-group insulin was strongly phase shifted in relation to the blood glucose excursions. In the TP-group, the Zucker rats were also hyperinsulinemic. Plasma insulin at 05.00 p.m. was significantly lower than in the RP (p<0.05 vs. RP). Parallel to blood glucose increases (FIG. IV/3A) there was an increase in plasma insulin at 08.00 p.m. (41.9±8.5 ng/ml). The maximum insulin value was measured at 05.00 a.m. (57.1±8.6 ng/ml; p<0.01 vs. initial values). The concentration of plasma insulin was lowered reaching basal concentration (24.3±3.7 ng/ml) at ca. 2.00 p.m. the next day which was significantly lower than in CO or RPgroups (p<0.01 vs. CO or TP).

Figure 5A:
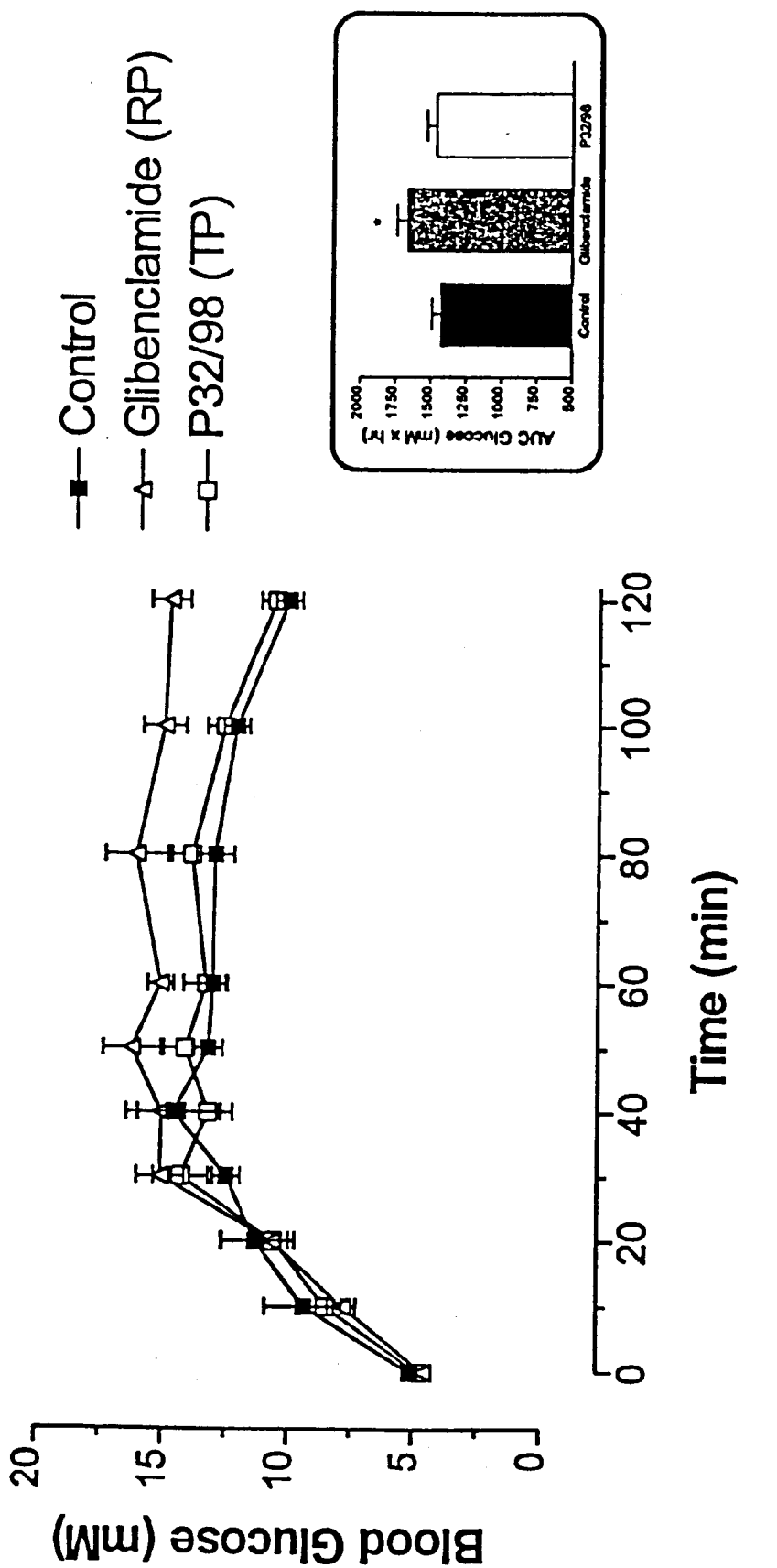
FIG. 5a is a graphical representation showing the blood glucose levels as a function of time in the maintenance of improved glycemia after 21 days of subchronic treatment of obese, diabetic fa/fa rats by the formulated DP IV-inhibitor p32/98.

OGTT after 21 days treatment, blood glucose curves (See FIG. 5A): The last drug application at 05.00 p.m. and overnight fasting on day 21 were followed by a significant decline in glycemia in the CO-group from 8.68±1.26 mmol/l (05.00 p.m.) to 5.08±0.24 mmol/l (p<0.05), in the RPgroup from 8.81±1.21 mmol/l to 4.91±0.37 mmol/l (p<0.01) and in the TP-group from 5.75±0.23 mmol/l to 4.88±0.13 mmol/l (p<0.01). For this reason oral glucose loads were performed from a comparable basal glucose concentration level in all three experimental groups found in the morning (07.30 a. m.).

In the CO-group glycemia increased after oral glucose application to peak values of 14.64±1.42 mmol/l within 40 min. Later there was a slight, significant decline to 9.75±0.46 mmol/l at the end of the test (120 min). In the RP-group, there was a steep increase to higher blood glucose values of 16.33±0.98 and 16.24±1.09 mmol/l at 50 min and 80 min, respectively. The high glucose concentrations were maintained until the end of study at 120 min (100 min: 15.13±0.76 mmol/l, 120 min: 14.81±0.66 mmol/l; NS from the former peak values). In the TP-group, similar properties of the mean blood glucose curve as in the CO-group were found. Glycemia increased to 14.54±0.65 mmol/l at 50 min and declined significantly to a value of 10.67±0.62 mmol/l (120 min; NS from CO).

The glucose area under the curve (G-AUC$_{0-120}$ min) in the CO- and TP-groups were 823±41 and 895±50 mmol-min/l, respectively (NS). In the RP-group this parameter was determined as 1096±76 mmol-min/l and that value was significantly higher than in CO- (p<0.01) or TP-groups p<0.05).

Figure 5B:
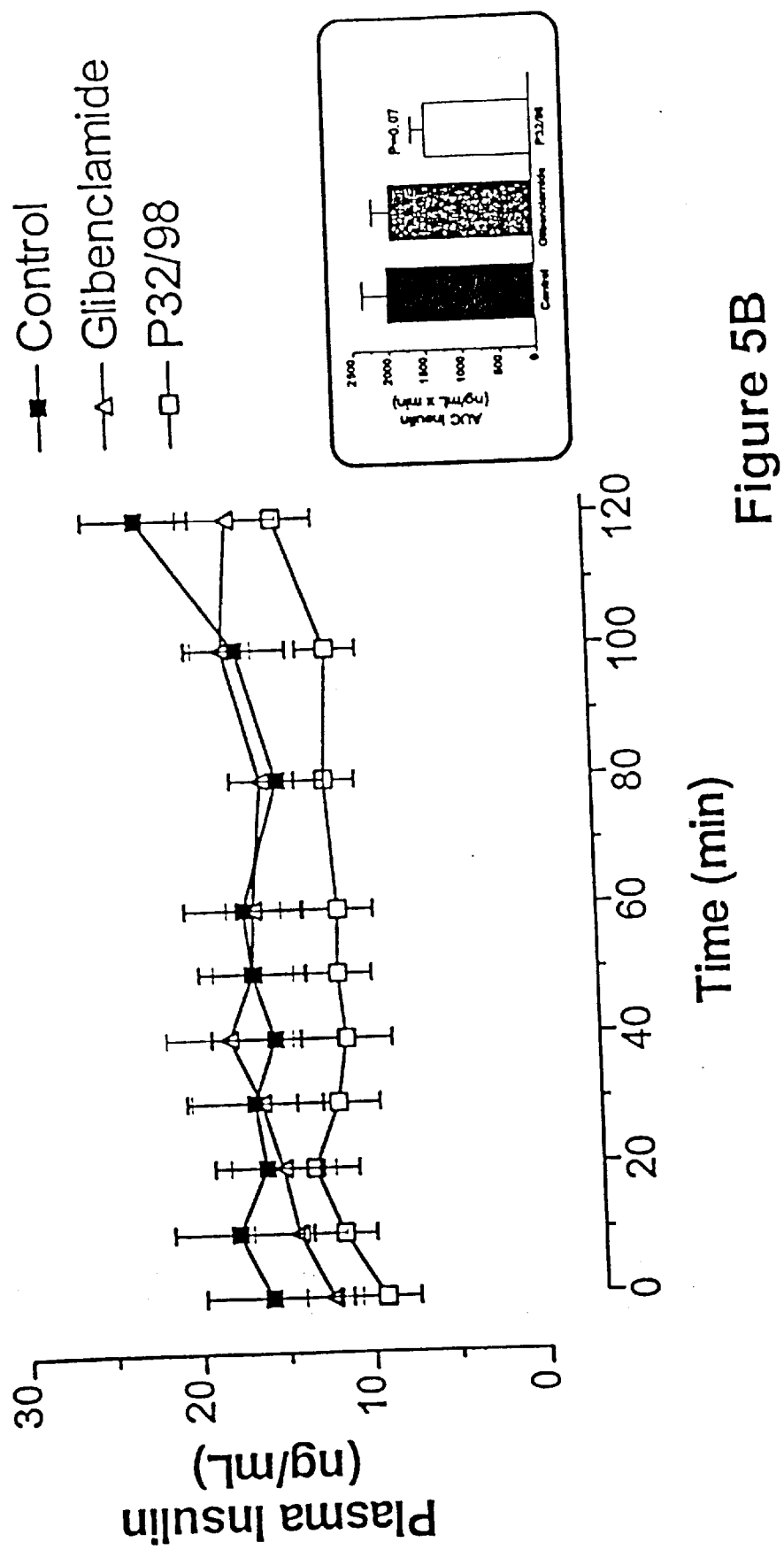
FIG. 5b is a graphical representation showing the plasma insulin levels as a function of time in the maintenance of improved glycemia after 21 days of sub-chronic treatment of obese, diabetic fa/fa rats by the formulated DP IV-inhibitor p32/98.

OGTT after 21 days treatment, plasma insulin (See FIG. 5B): Overnight fasting in the Zucker rats led to reduced plasma insulin concentrations in the CO-animals (14.6±3.7 ng/ml), in the RP-group to 11.8±1.5 ng/ml, and in the TP-group to 9.3±1.5 ng/ml, respectively. The differences between experimental groups were not significant. After a glucose stimulus, plasma insulin remained mostly unchanged in the CO-, RP- and TP-groups. Slightly higher values were found at 120 min in the CO-group only, amounting to 21.3±3.0 ng/ml, which was significantly higher than in the TP-group (p<0.05).

The I-AUC$_{0-120}$ min was generally low. In the TP-group this parameter was lower than in the CO- or RP-groups (NS).

Summary

Morning blood glucose: The placebo treated controls were hyperglycemic (about 7.5 mmol/l).

The mean concentration was unchanged during the study. RP therapy increased blood glucose by about 1.5 mmol/l within two days. Glycemia remained in the higher range. TP-medication reduced blood glucose to a normal value within 5 days. Blood glucose remained in the normal range up to the end of the study.

Plasma insulin: The control Zucker rats were hyperinsulinemic and showed some further insulin increase during the 14 days of observation. The RP-treated Zucker rats showed an insulin increase to significantly higher concentrations than in control animals. The TP application did slightly decrease insulin concentration for 14 days in comparison to the control animals.

OGTT after 21 days treatment blood glucose: Overnight fasting reduced blood glucose to normal values in the experimental groups. The placebo-treated animals showed about a 9 mmol/l blood glucose increase within 40 min after the glucose load and a slight decline thereafter. RP-treated Zucker rats showed a about 11 mmol/l blood glucose increase after the glucose load with no decline during the test. The mean blood glucose curve of the TP-treated animals was not different from that of the controls. The RP-treatment increased the G-AUC, the TP-medication did not increase G-AUC in comparison to the placebo application.

OGTT after 21 days treatment, plasma insulin: The control Zucker rats had the highest fasting insulin of the three experimental groups of about 15 ng/ml. After the glucose load, insulin increased significantly only at the end of the test (120 min). The RP-treated rats had some lower fasting insulin of ~12.5 ng/ml at the beginning of the OGTT and an earlier increase at 40 min with no decline at the end of the test. The TP-treated rats had the lowest fasting insulin of ~9 ng/ml at the beginning of the OGTT, an early modest increase at 20 min in relation to the blood glucose rising and lowered concentrations between 40 min and 100 min. The I-AUC was slightly lower in the TP-treated rats.

Conclusion

The DP IV inhibitor P32/98 (TP), given once daily, normalized morning blood glucose, reduced hyperinsulinemia, held blood glucose in the day-night profile below the (for diabetic patients) critical 8.3 mmol/l. The metabolic benefit was retained a limited time after cessation of P32/98 medication.

What is claimed is:

1. A method for increasing the capacity of insulin providing cells in an animal comprising administering to said animal a therapeutically effective dose of at least one DP IV enzyme activity effector.

2. The method of claim 1 wherein said increasing the capacity of insulin producing cells comprises causing endogenous insulin producing cells to become more effective insulin producers.

3. The method of claim 1 wherein said increasing the capacity of insulin producing cells comprises causing cells present in the pancreas to differentiate into insulin producing cells.

4. The method of claim 1 wherein said DP IV effector is selected from the group consisting of N-(N'-substituted glycyl)-2-cyanopyrrolidines, N-aminoacyl thiazolidines, N-aminoacyl pyrrolidines: such as L-threo-isoleucyl thiazolidine (P32/98), L-allo-isoleucyl thiazolidine, L-threo-isoleucyl pyrrolidine, and L-allo-isoleucyl pyrrolidine and pharmaceutical salts thereof.

5. The method of claim 1 wherein said effector comprises a substrate capable of binding with said DP IV and which competes with naturally occurring substrates for DP IV.

6. The method of claim 1 wherein said administration comprises oral administration.

7. The method of claim 1 wherein said administration comprises iv or im injection.

8. The method of claim 1 wherein said administration comprises chronic oral administration.

9. The method of claim 1 wherein said administration comprises chronic iv or im injection.

10. The method of claim 1 further comprising the administration of glucose or the intake of food takes place before, during or after the administration of said DP IV activity effector.

11. The method of claim 8 wherein said administration of said DP IV activity effector occurs before said administration of glucose, or intake of food.

* * * * *

(12) EX PARTE REEXAMINATION CERTIFICATE (6215th)
United States Patent
Demuth et al.

(10) Number: US 6,500,804 C1
(45) Certificate Issued: Apr. 29, 2008

(54) METHOD FOR THE IMPROVEMENT OF ISLET SIGNALING IN DIABETES MELLITUS AND FOR ITS PREVENTION

(75) Inventors: Hans-Ulrich Demuth, Halle (DE); Konrad Glund, Halle (DE)

(73) Assignee: Probiodrug AG, Halle/Saale (DE)

Reexamination Request:
No. 90/006,954, Mar. 1, 2004

Reexamination Certificate for:
Patent No.: 6,500,804
Issued: Dec. 31, 2002
Appl. No.: 09/824,622
Filed: Apr. 2, 2001

Related U.S. Application Data

(60) Provisional application No. 60/194,061, filed on Mar. 31, 2000.

(51) Int. Cl.
*A61K 31/00* (2006.01)
*A61K 45/00* (2006.01)
*A61K 45/06* (2006.01)
*A61K 31/40* (2006.01)
*A61K 31/426* (2006.01)

(52) U.S. Cl. .................. 514/19; 514/365; 514/866

(58) Field of Classification Search ............... None
See application file for complete search history.

(56) References Cited

FOREIGN PATENT DOCUMENTS

| DE | 299 09 210 U | 9/1999 |
|---|---|---|
| WO | WO 98/19998 | 5/1998 |

OTHER PUBLICATIONS

Pederson, R.A., et al., "Improved Glucose Tolerance in Zucker Fatty Rats by Oral Administration of the Dipeptidyl Peptidase IV Inhibitor Isoleucine Thiazolidide", *Diabetes*, vol. 47, Aug. 1998 pp. 1253–1258.

*Primary Examiner*—Dwayne C. Jones

(57) ABSTRACT

The present invention discloses a method for therapeutically treating mammals, including but not limited to humans, to increase the relative insulin producing performance of endogenous pancreatic β-cells and to cause differentiation of pancreatic epithelial cells into insulin producing β-cells. Oral administration a DPIV inhibitor causes the active form of GLP-1 to be preserved longer under physiological conditions. The extended presence of GLP-1, in particular in the pancreatic tissue facilitates differentiation and regeneration of the β-cells already present that are in need of repair. These repaired insulin producing cells can contribute to the correction and maintenance of normal physiological glycemic levels.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–11 are cancelled.

* * * * *